United States Patent
Prasad et al.

(10) Patent No.: US 11,293,898 B2
(45) Date of Patent: Apr. 5, 2022

(54) DUTY CYCLE IMPROVEMENT FOR A MASS SPECTROMETER USING ION MOBILITY SEPARATION

(71) Applicant: Thermo Finnigan LLC, San Jose, CA (US)

(72) Inventors: Satendra Prasad, San Jose, CA (US); Eloy R. Wouters, San Jose, CA (US); Jean-Jacques Dunyach, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 239 days.

(21) Appl. No.: 16/784,135

(22) Filed: Feb. 6, 2020

(65) Prior Publication Data

US 2021/0247359 A1 Aug. 12, 2021

(51) Int. Cl.
| | | |
|---|---|---|
| *G01N 27/624* | (2021.01) | |
| *G01N 27/622* | (2021.01) | |
| *G01N 30/72* | (2006.01) | |
| *G01N 33/68* | (2006.01) | |
| *H01J 49/04* | (2006.01) | |
| *H01J 49/16* | (2006.01) | |
| *G01N 30/02* | (2006.01) | |

(52) U.S. Cl.
CPC ....... *G01N 27/622* (2013.01); *G01N 30/7233* (2013.01); *G01N 33/68* (2013.01); *H01J 49/0431* (2013.01); *H01J 49/165* (2013.01); *G01N 2030/027* (2013.01)

(58) Field of Classification Search
CPC .. G01N 27/622; G01N 30/7233; G01N 33/68; G01N 2030/027; G01N 27/623; G01N 27/624; H01J 49/0431; H01J 49/165; H01J 49/004; H01J 49/42; H01J 49/066; H01J 49/282

See application file for complete search history.

(56) References Cited

U.S. PATENT DOCUMENTS

| | | | |
|---|---|---|---|
| 7,462,825 B2 | 12/2008 | Miller et al. | |
| 8,507,852 B2 | 8/2013 | Makarov | |
| 9,305,762 B2 | 4/2016 | Covey et al. | |
| 9,753,011 B2 | 9/2017 | Makarov | |
| 10,281,426 B2 * | 5/2019 | Green ................ | H01J 49/0404 |
| 10,788,449 B2 | 9/2020 | Green et al. | |
| 2003/0001084 A1 * | 1/2003 | Bateman ............. | H01J 49/4215 |
| | | | 250/281 |

(Continued)

FOREIGN PATENT DOCUMENTS

| | | |
|---|---|---|
| EP | 2001039 A1 | 12/2008 |
| EP | 2425446 B1 | 3/2012 |
| EP | 2455963 A2 | 5/2012 |

OTHER PUBLICATIONS

EP Extended Search Report dated Jul. 8, 2021, to EP Patent Application No. 21155242.7.

(Continued)

*Primary Examiner* — David J Bolduc

(57) ABSTRACT

Using ion mobility separation to improve a duty cycle of a mass spectrometer is described. In one aspect, a mass spectrometer can use an ion-mobility spectrometer to allow for more multiply-charged ions to transmit through than singly-charged ions. This results in a mass analyzer to perform a mass analysis with more multiply-charged ions.

20 Claims, 10 Drawing Sheets

(56) References Cited

U.S. PATENT DOCUMENTS

| | | | |
|---|---|---|---|
| 2009/0294662 A1* | 12/2009 | Belov | H01J 49/4235 250/291 |
| 2011/0253890 A1* | 10/2011 | Belford | G01N 27/624 250/288 |
| 2011/0260048 A1* | 10/2011 | Wouters | H01J 49/0404 250/282 |
| 2012/0153140 A1* | 6/2012 | Makarov | G01N 27/622 250/282 |
| 2015/0008318 A1* | 1/2015 | Makarov | G01N 27/622 250/283 |
| 2015/0362461 A1* | 12/2015 | Prasad | H01J 49/0031 250/283 |
| 2016/0077054 A1* | 3/2016 | Giles | G01N 27/622 250/282 |
| 2016/0084799 A1* | 3/2016 | Makarov | H01J 49/0031 250/283 |
| 2016/0118234 A1* | 4/2016 | Covey | H01J 49/165 250/282 |
| 2017/0338093 A1* | 11/2017 | Green | G01N 27/622 |
| 2018/0038821 A1 | 2/2018 | Ibrahim et al. | |
| 2018/0038831 A1* | 2/2018 | Ibrahim | H01J 49/425 |

OTHER PUBLICATIONS

Ibrahim et al, "New Frontiers for Mass Spectrometry based upon Structures for Lossless Ion Manipulations", Analyst, vol. 142, pp. 1010-1021 (2017).

Ibrahim et al., "Ion Elevators and Escalators in Multilevel Structures for Lossless Ion Manipulations", Analytical Chemistry, vol. 89, pp. 1972-1977 (2017).

Swearingen et al. "High-field Asymmetric Waveform Ion Mobility Spectrometry for Mass Spectrometry-based Proteomics" Expert Rev Proteomics, Oct. 2012, vol. 9, Issue 5, pp. 505-517.

Jensen et al., "A Compact Quadrupole-Orbitrap Mass Spectrometer with FAIMS Interface Improves Proteome Coverage in Short LC Gradients," Moll Cell Proteomics Papers, Published Feb. 12, 2020, 31 pages.

Barnett et al., "Application of ESI-FAIMS-MS to the Analysis of Tryptic Peptides," Journal of the American Society for Mass Spectrometry, Nov. 2002, vol. 13, Issue 11, pp. 1282-1291.

\* cited by examiner

DUTY CYCLE IMPROVEMENT FOR A MASS SPECTROMETER USING ION MOBILITY SEPARATION

TECHNICAL FIELD

This disclosure relates to mass spectrometry, and more particularly to using ion mobility separation to improve a duty cycle of a mass spectrometer.

BACKGROUND

A current focus of biological mass spectrometry is the identification, quantification, and structural elucidation of peptides, proteins, and related molecules. In the context of bottom-up proteomics experiments, proteins are subject to proteolytic digestion to break down into fragments of peptides which are then separated, usually with liquid chromatography (LC), before being introduced into an ion source of a mass spectrometer. Typically, the ion source for proteomics experiments implements electrospray ionization (ESI) to ionize the peptide. ESI of peptide-containing samples will typically produce both singly and multiply charged ions. That is, the ions include singly charged ions (e.g., +1), and multiply charged ions including doubly charged ions (e.g., +2), triply-charged ions (e.g., +3), and so forth of the peptide. Often, singly-charged ions will comprise a substantial portion or even a preponderance of the total.

Singly charged ions are generally of less interest in bottom-up proteomics experimentation as the singly charged ions are often the result of sample preparation, contamination, or other scenarios. The interesting information regarding the biologically significant peptides is obtained from analysis of the multiply charged ions.

In certain pulsed mass analyzers, such as an orbital electrostatic trap mass analyzer (commercially available from Thermo Fisher Scientific under the trademark "Orbitrap"), mass analysis is performed by storing ions produced by ESI in a storage trap and then transferred into the orbital electrostatic trap for mass analysis. The number of ions stored within the storage trap (or more specifically, the aggregate number of charges) is limited to a target that is determined in part by the storage trap geometry and dimensions. When the target number has been attained, the storage trap is switched to a closed state in which no additional ions are permitted to enter the storage trap. Because a significant portion of the total number of ions stored in the trap for subsequent mass analysis is represented by singly-charged ions, the number of (more analytically significant) multiply charged ions available for analysis is reduced, leading to decreased sensitivity. Furthermore, because the storage trap reaches capacity relatively quickly due to the presence of large numbers of singly-charged ions, much of the ions produced by the ion source are wasted. This reduces the duty cycle (i.e., the fraction of ions of interest produced by the ion source that are mass analyzed) of the mass spectrometer.

SUMMARY

One innovative aspect of the subject matter described in this disclosure includes an apparatus for analyzing a peptide-containing biological sample including: a chromatography device configured to temporally separate components of the biological sample; an electrospray ionization (ESI) source configured to receive a component separated from the biological sample and generate singly-charged ions and multiply-charged ions from the component; a field asymmetric-waveform ion-mobility spectrometry (FAIMS) device configured to receive the singly-charged ions and the multiply-charged ions, and preferentially transmit multiply-charged ions; an ion accumulator arranged to receive and confine the ions transmitted by the FAIMS device; a storage trap configured to receive the ions released from the ion accumulator and store the released ions, the storage trap having a lower storage capacity than the ion accumulator; a mass analyzer configured to receive the ions stored in the storage trap for mass analysis; and a controller circuit configured to adjust operation of the accumulator to allow release a portion of the ions confined therein to the storage trap.

In some implementations, the storage trap is a curved linear ion trap, and the mass analyzer is an orbital electrostatic trap mass analyzer.

In some implementations, the ion accumulator is an ion funnel.

Another innovative aspect of the subject matter described in this disclosure includes a mass spectrometer including: an ion source configured to receive a sample and generate singly-charged ions and multiply-charged ions from the sample; an ion-mobility spectrometer (IMS) configured to receive the singly-charged ions and the multiply-charged ions, and configured to allow transmission of more multiply-charged ions through an output of the IMS than transmission of the singly-charged ions through the output of the IMS; an ion accumulator configured to store the multiply-charged ions that drift through the output of the IMS; a storage trap configured to receive a portion of the multiply-charged ions stored by the ion accumulator; a mass analyzer configured to receive the portion of multiply-charged ions stored in the storage trap for mass analysis; and a controller circuit configured to determine an operational state of the mass analyzer and adjust operation of the ion accumulator to allow the portion of the multiply-charged ions to transmit from the ion storage to the storage trap.

In some implementations, the storage trap is a curved linear ion trap, and the mass analyzer is an orbital electrostatic trap mass analyzer.

In some implementations, the IMS is a field asymmetric-waveform ion-mobility spectrometer (FAIMS), and the transmission of the multiply-charged ions through the output is based on an application of a range of compensation voltages (CVs) applied to an electrode of the FAIMS that causes the multiply-charged ions to drift through to the output without impacting an electrode of the FAIMS and causes the singly-charged ions to impact an electrode of the FAIMS without drifting through the output.

In some implementations, the ion accumulator is an ion funnel.

In some implementations, the operational state of the mass analyzer is one of: currently performing mass analysis, or available to perform mass analysis, and wherein the operation of the ion funnel is adjusted to store the multiply-charged ions without transmitting the multiply-charged ions from the ion funnel to the ion trap when the operational state of the mass analyzer is currently performing mass analysis, and the operation of the ion funnel is adjusted to store the multiply-charged ions while allowing transmitting of the multiply-charged ions from the ion funnel to the ion trap when the operational state of the mass analyzer is available to perform mass analysis.

In some implementations, the controller circuit is configured to allow transmission of the portion of the multiply-charged ions stored in the ion accumulator to the storage trap based on a determination of the operational state of the mass analyzer indicating that the mass analyzer is available to perform mass analysis.

In some implementations, the ion accumulator is an ion funnel.

In some implementations, the mass spectrometer includes a separation device configured to separate the sample from a mixture, wherein the controller circuit is further configured to determine information related to how the sample is separated from the mixture, and wherein the controller is configured to adjust operational parameters of the IMS based on the determination of the information related to how the sample is separated from the mixture.

In some implementations, the IMS is a field asymmetric-waveform ion-mobility spectrometer (FAIMS), and the operational parameters are compensation voltages (CVs) applied to an electrode of the FAIMS.

In some implementations, the mass spectrometer includes a chromatography system configured to separate the sample from a mixture, wherein the controller circuit is further configured to determine a retention time of the sample, and wherein the controller is configured to adjust operational parameters of the IMS based on the determination of the retention time of the sample.

In some implementations, the chromatography system is a liquid chromatography (LC) system.

Another innovative aspect of the subject matter described in this disclosure includes a method of operating a mass spectrometer to analyze a biological sample, including: ionizing a sample to generate singly-charged ions and multiply-charged ions from the biological sample; transmitting more of the multiply-charged ions than the singly-charged ions; storing the multiply-charged ions in an ion accumulator, the ion accumulator storing more multiply-charged ions than singly-charged ions; determining that a mass analyzer is available to perform mass analysis; transmitting a portion of the multiply-charged ions from the ion accumulator to a storage trap based on the determination that the mass analyzer is available to perform mass analysis; injecting the portion of the multiply-charged ions from the storage trap to the mass analyzer; and performing a mass analysis of the portion of the multiply-charged ions.

In some implementations, transmitting more of the multiply-charged ions than the singly-charged ions includes: receiving, with a field asymmetric-waveform ion-mobility spectrometer (FAIMS), the singly-charged ions and the multiply-charged ions; and applying a range of compensation voltages (CVs) to an electrode of the FAIMS to cause the multiply-charged peptide ions to drift through to the output without impacting an electrode of the FAIMS and causes the singly-charged peptide ions to impact an electrode of the FAIMS without drifting through the output.

In some implementations, the biological sample is a mixture of peptides.

In some implementations, the mass analyzer is an orbital electrostatic trap mass analyzer.

In some implementations, the ion accumulator is an ion funnel.

In some implementations, the storage trap is a curved linear ion trap.

DETAILED DESCRIPTION

Figure 1:
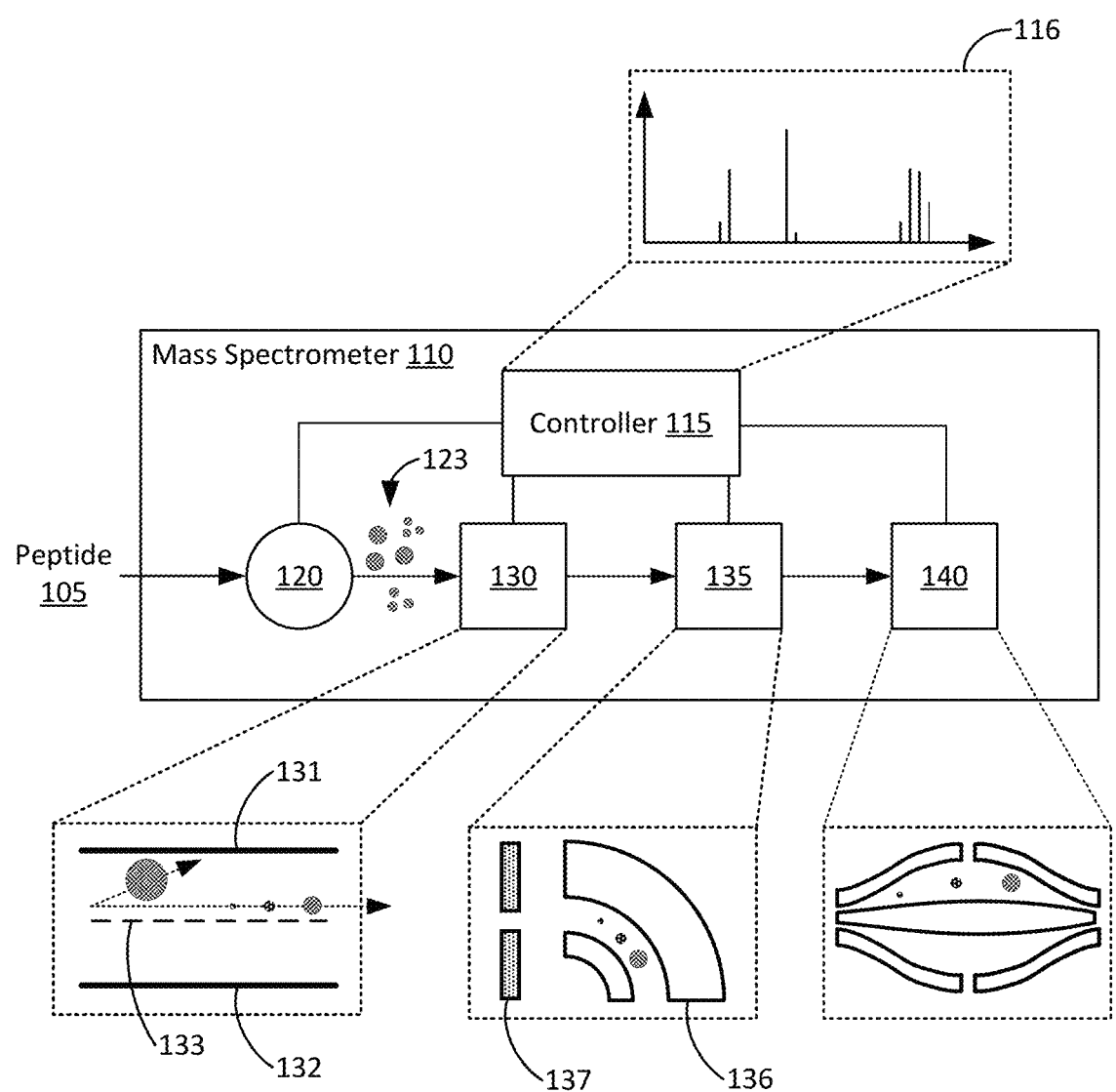
FIG. 1 illustrates an example of a mass spectrometer using ion mobility separation to increase the abundance of multiply charged ions used in mass analysis.

Some of the material described in this disclosure includes mass spectrometers and techniques for using ion mobility separation to improve the duty cycle of a mass spectrometer. As used herein, the term "ion mobility separation" and its variants include any device or technique in which ions are separated or filtered on the basis of their mobility properties, and is intended to embrace both conventional ion mobility separation devices such as a drift tube in which ions travel through a drift gas at a rate determined by their mobilities, as well as differential mobility devices (such as the FAIMS device described below), in which ions are separated or filtered in accordance with their ratios of high field to low field mobilities.

In one example, a mixture including peptides is introduced into a chromatography system such that different peptides in the mixture are separated and introduced into a mass spectrometer for analysis at different times. As a peptide is introduced into the mass spectrometer, the peptide and other co-eluting substances are ionized using electrospray ionization (ESI) to produce ions that are transported among the components of the mass spectrometer for mass analysis. Unfortunately, many of the ions produced using ESI with peptide-containing samples are singly charged ions that are less useful for proteomics experimentation than multiply charged ions.

As described later in this disclosure, ion mobility separation can be performed following the production of the ions by the ion source, but before storage of the ions in the storage trap. The ion mobility separation prevents or substantially reduces the transmission of the singly charged ions while allowing transmission of the multiply charged ions, resulting in the ions used for mass analysis to include more of the ions that are of analytical interest. For example, the ion mobility separation can be performed by a field asymmetric-waveform ion-mobility spectrometry (FAIMS) device using a compensation voltage (CV) range that only or mostly allows the multiply charged ions to transmit through. By preventing, or reducing, the transmission of the singly charged ions to the storage trap, more of the ions accumulated in the storage trap are multiply charged ions. This improves the quality of the data acquired via the mass analysis. Moreover, this also improves the duty cycle of the mass spectrometer.

Additionally, ions can also be stored in an ion accumulator (storage, e.g., an ion funnel) disposed between the ion mobility separation device and the storage trap. That is, while the storage trap is closed, ions can be trapped and stored in the accumulator. When the storage trap is opened again, the ion accumulator allows a portion of the stored ions to transmit to storage within the storage trap. When the storage trap reaches capacity, the storage trap is closed again, the stored ions are transmitted from the storage trap to the orbital electrostatic trap, and the accumulator is closed to prevent transmission of ions, resulting in the ions being stored within the accumulator. This results in more of the ions available for mass analysis, which also improves the duty cycle and the quality of the data acquired.

Also described later in this disclosure is synchronizing the operation of the FAIMS device, another ion mobility spectrometry (IMS) device, and an orbital electrostatic trap. When the orbital electrostatic trap begins performing a mass analysis, this can trigger adjusting the CV of the FAIMS device and allow the IMS device to begin filtering ions.

Also described later in this disclosure, information regarding how the peptide is separated in a mixture using the LC system can also be determined and provided to the mass spectrometer. This information can be used to modify the CV of the FAIMS device, further improving the transmission of multiply charged ions.

Figure 2:
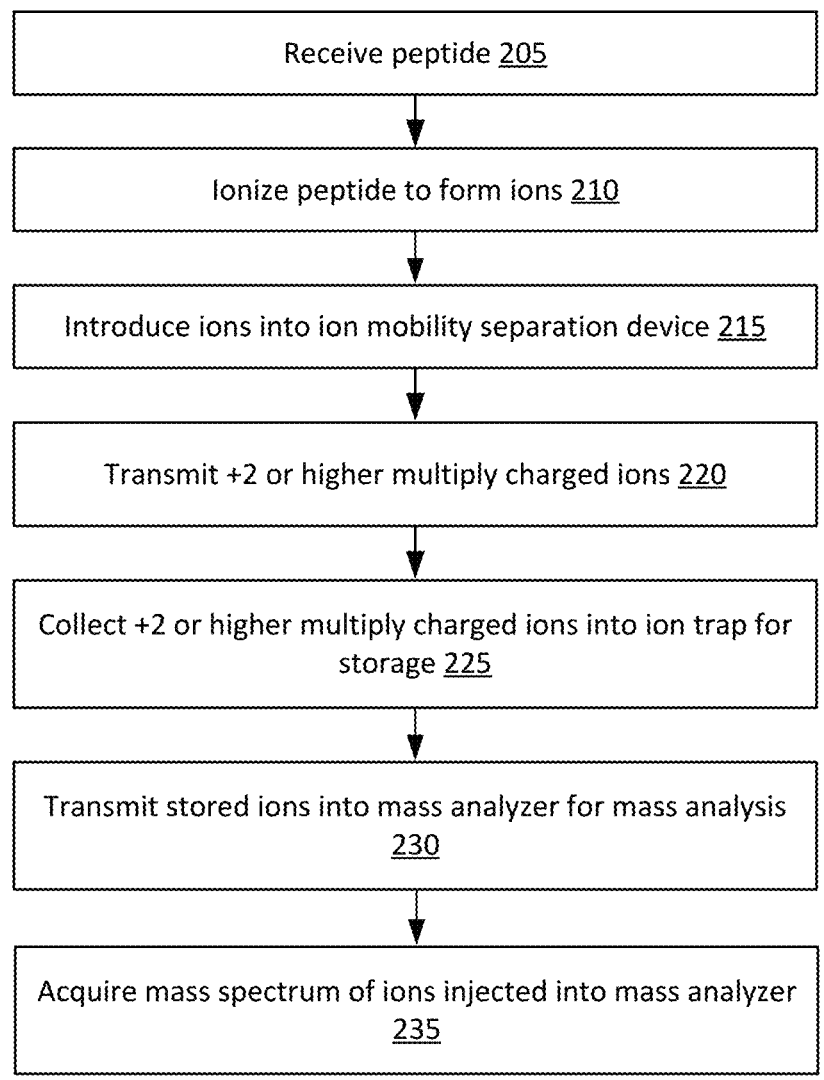
FIG. 2 illustrates an example of a block diagram for operating a mass spectrometer using ion mobility separation to increase the abundance of multiply charged ions used in mass analysis.

In more detail, FIG. 1 illustrates an example of a mass spectrometer using ion mobility separation to increase the abundance of multiply charged ions used in mass analysis. FIG. 2 illustrates an example of a block diagram for operating the mass spectrometer of FIG. 1. In the block diagram of FIG. 2, a peptide is provided to a mass spectrometer (205). For example, in FIG. 1, peptide 105 is a peptide separated from other peptides (and other components) in a mixture using liquid chromatography (LC), gas chromatography (GC), capillary electrophoresis (CE), or other type of system used to separate components of a mixture. In the example of proteins subject to digestion, the separate components of the mixture are peptides (e.g., fragments of the protein).

Returning to FIG. 2, the peptide is then ionized to form ions (210). In FIG. 1, this is depicted as peptide 105 being introduced into ion source 120 of mass spectrometer 110. Ion source 120 ionizes a material under analysis (i.e., peptide 105) by removing or adding charge-carrying entities (e.g., hydrogen nuclei or electrons) to or from the material to provide the material with a positive or negative charge. This results in ions 123 forming from the ionization of peptide 105. Ion source 120 is usually of the ESI type, but may instead utilize any other suitable ionization technique, including atmospheric-pressure chemical ionization (APCI) or atmospheric pressure photoionization (APPI). As described above, ionization of the peptide-containing sample will typically produce both singly charged ions (which will include the +1 state of the peptide as well as interfering species such as solvent clusters) and multiply charged ions.

In the block diagram of FIG. 2, the ions produced by the ion source are then introduced into an ion mobility separation device (215) and the multiply charged ions are preferentially transmitted relative to the singly charged. For example, in FIG. 1, ion mobility separation device 130 separates ions based on their mobility properties in the presence of a buffer gas and exposure to an electric field. That is, rather than separating ions based on a mass-to-charge ratio, ion mobility separation device 130 separates ions by their mobility properties (e.g., their mobilities in a fixed field, or the ratio of their high field to low field mobilities. In FIG. 1, this is implemented using a high-field asymmetric waveform ion mobility spectrometry (FAIMS) device that is used as a filter.

A FAIMS device is depicted in a simplified example in FIG. 1 as having two parallel plates with electrode 131 and electrode 132, but some implementations include different geometries such as electrodes 131 and 132 as cylindrical electrodes with one disposed or positioned within the other electrode. Electrode 132 can be grounded (e.g., at 0 V) while a high-voltage asymmetric radio frequency (RF) signal is applied to electrode 131, or vice versa. The signal applied to electrode 131 is composed of two sine waves with different phases (e.g., one ninety degrees out-of-phase from the other) and different amplitudes such that they define a first portion that has a higher positive amplitude than a negative amplitude of a second portion (e.g., the first portion might range from 0 volts (V) to X V whereas the second portion might range from 0 V to −0.5X V), but the first portion is asserted for a shorter time period than the second portion (e.g., the first portion might be asserted for t microseconds (μs) and the second portion might be asserted for 2t μs). This results in the ions introduced into and transmitting within ion mobility separation device 130 to be subjected to an electric field that is higher-strength in one direction for a shorter period of time, but then switched to an electric field that is lower-strength in a second another direction for a longer period of time. Based on the differential mobilities of the ions in the different higher-strength and lower-strength electric fields, ions will generally drift towards one of the electrodes as they pass through ion mobility separation device 130. In other types of IMS, mobility separates ions (due to the electric field not changing), whereas in FAIMS, the ions separate due to differences in mobility caused by the changing electric field. For example, during the lower-strength field, ions can drift similar to other types of IMS, but in the higher-strength electric field, ions drift due to a differential mobility that adds up via the periodicity of the RF signal. Thus, in IMS devices (including FAIMS), the mobility properties or characteristics causes ions to be separated or filtered.

To account for the drift and allow selected ions to be able to transmit through without hitting one of the electrodes, a DC compensation voltage (CV) is applied to electrode 131. The application of the CV counteracts the ion drift arising from the oscillatory field such that ions generally track path 133 and exit the ion separation device 130. If an appropriate CV is applied to electrode 131, then one type of ion might drift to and from path 133 but be able to transmit through ion mobility separation device 130. By contrast, if the CV applied does not correct for enough of the drift of another ion, then that ion might drift to and from path 133, but overall drift closer to one of the electrodes and eventually impact an electrode, thus resulting in that ion not transmitting through ion mobility separation device 130. By scanning through multiple CV values (i.e., applying CVs within a range of CVs), ions can be filtered through ion mobility separation device 130 in accordance with their relative mobilities. If the CV range does not include a CV for an ion with a particular relative mobility to transmit through, then ion mobility separation device 130 effectively acts as a filter.

As previously discussed, ion source 120 might implement ESI which forms singly charged ions and multiply charged ions. The singly charged ions are of less analytical interest in comparison to the multiply charged ions. Filtering out the singly charged ions using ion mobility separation device 130 can allow for more multiply charged ions to be mass analyzed. Thus, in FIG. 1, to enable transmission of the multiply charged ions with reduced transmission of the singly charged ions can be performed by using a CV range that results in fewer, or even none, of the singly charged ions to transmit through while the multiply charged ions transmit through using the CV range. This results in more of the multiply charged ions to transmit through than the amount of singly charged ions that transmit through.

In some implementations, a conventional ion mobility separation device (e.g., ones using drift tubes) can employ gating mechanisms to separate, and even filter out singly charged ions from the multiply charged ions.

Figure 3:
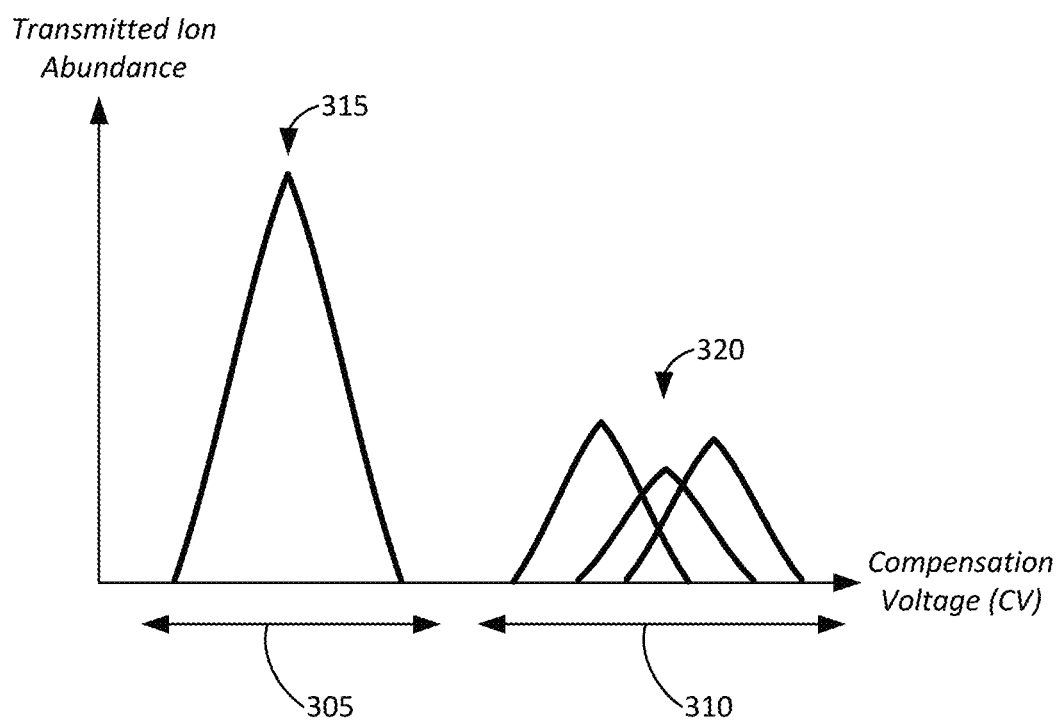
FIG. 3 illustrates an example of compensation voltages (CVs) used for ion mobility separation of singly charged ions and multiply charged ions.

FIG. 3 illustrates an example of compensation voltages (CVs) used for ion mobility separation of singly charged ions and multiply charged ions. In FIG. 3, peak 315 represents the transmission of singly charged ions and peaks 320 represent the transmission of multiply charged ions. CV range 305, for example, can range from −10 V to −30 V while CV range 310 can range from −40 V to −80 V. As depicted in FIG. 3, peaks 320 are clustered and overlapping in ion transmission at CV voltages within CV range 310. However, the ion transmission for peak 315 is not within CV range 310 and, therefore, singly charged ions would not transmit through ion mobility separation device 130 if CV voltages within CV range 310 are applied to electrode 131 and CV voltages within CV range 305 are not applied to electrode 131. In one implementation, the CV voltages within CV range 305 might step from −50 V to −60 V to −80 V. Alternating or incrementing the CV voltages among these three voltages, and repeating the sequence of CV voltages, allows for multiply charged ions of peptides to transmit while the singly charged ions do not transmit. However, FIG. 3 is an idealized example, and in other scenarios some singly charged ions can transmit, and the peaks of FIG. 3 can overlap including peak 315 overlapping with one or more peaks representing the multiply-charged ions.

As a result, all or a substantial portion of the singly charged ions (represented by the larger circles in ions 123 in FIG. 1) are not transmitted through ion mobility separation device 130 whereas all or a substantial portion of multiply charged ions (represented by the smaller circles in ions 123) are transmitted through. That is, more multiply-charged ions are transmitted through in comparison with singly charged ions. The transmitted multiply charged ions are therefore collected into an ion trap for storage (225 in FIG. 2). This is depicted in FIG. 1 as ions being stored in ion trap 135, which can be implemented with storage trap 136. In the implementation of FIG. 1, ions are introduced into the storage trap by passing through split lens 137, which governs the introduction of transmitted ions into storage trap 136 based on a voltage applied. That is, split lens 137 provides ion gating to allow or disallow the transmission of ions into storage trap 136.

Storage trap 136 may be a curved linear ion trap that stores a population of ions corresponding to a maximum aggregate number of charges. When storage trap 136 is filled with the appropriate number of charges (e.g., as determined by the rate of ions transmitting from ion mobility separation device 130), the operation of split lens 137 can be adjusted (e.g., by changing a voltage applied to it) such that ions are now no longer allowed to be transmitted into storage trap 136.

Next, in FIG. 2, the ions stored in the ion trap are transmitted to a mass analyzer for mass analysis (230). For example, in FIG. 1, the multiply charged ions in storage trap 136 are transmitted from storage trap 136 to orbital electrostatic trap 140, which is an orbital electrostatic trap, as previously discussed. Storage trap 136 may be defined by a curved central axis between electrodes (of which RF signals are applied) with a slot in the electrode closest to orbital electrostatic trap 140. This type of storage trap can also be referred to as a C-trap. When the multiply charged ions are accumulated within storage trap 136, the ions are "cooled" down via collisional cooling of ions with a gas such as nitrogen. Upon sufficient collisional cooling, the RF signal is quickly ramped down, resulting in the multiply charged ions being no longer confined by the RF field of storage trap 136. With the application of appropriate DC potentials applied to the storage trap electrodes and lenses arranged between storage trap 136 and orbital electrostatic trap 140, the multiply charged ions are then quickly moved towards the slot in the electrode closest to orbital electrostatic trap 140 and enter an aperture on an outer electrode of orbital electrostatic trap 140. Thus, the multiply charged ions are injected into orbital electrostatic trap 140 in a relatively quick time.

In FIG. 2, the ions injected into the mass analyzer are then analyzed to acquire a mass spectrum (235). In FIG. 1, orbital electrostatic trap 140 includes an internal central electrode with a spindle-like shape and outer electrodes enclosing the internal central electrode. Ions stored in storage trap 136 are injected into orbital electrostatic trap 140 such that the ions are in orbit around the central electrode and oscillate back-and-forth along the central electrode. The frequency of the longitudinal oscillatory motion of an ion species is a function of its mass-to-charge ratio and, therefore, an image current can be detected using the outer electrodes to determine the mass-to-charge ratios of the ions within orbital electrostatic trap 140 (e.g., using digital signal processing techniques such as Fourier transforms), resulting in controller 115 generating data that can be used to generate mass spectrum 116, which depicts the mass-to-charge ratios and abundances of ions at those ratios.

Because all or a substantial portion of the singly charged ions are filtered out by ion mobility separation device 130, relatively more multiply charged ions are stored within storage trap 136 and injected into orbital electrostatic trap 140, resulting in mass spectrum 116 including information related primarily to multiply charged ions rather than singly charged ions.

In the aforementioned example, storage trap 136 has a relatively small storage capacity (i.e., the number of ions that can be trapped therein without incurring space charge effects, which is a function of the trap dimensions and geometry) and can fill to a threshold level or capacity relatively quickly. For example, if both singly charged ions and multiply charged ions are allowed to enter storage trap 136 (i.e., ion mobility separation device 130 is not used between ion source 120 and ion trap 135), it might quickly fill to a maximum set threshold within 1 millisecond (ms) due to the relatively high number of singly charged ions. However, mass analysis using orbital electrostatic trap 140 might be accomplished within 60 ms. Thus, for 59 ms, during an analysis cycle, ions are generated by ion source 120, but the ions might not be allowed to transmit into storage trap 136 by split lens 137. Accordingly, a significant number of ions are wasted and not used for mass analysis. In this example, a duty cycle of mass spectrometer 110 is 1 ms/60 ms. By filtering out the singly charged ions using ion mobility separation device 130 implementing FAIMS, storage trap 136 might fill in 10 ms due to the lower number of multiply charged ions generated by ion source 120. This increases the duty cycle of mass spectrometer 110 to 10 ms/60 ms, which is a significant improvement.

Figure 4A:
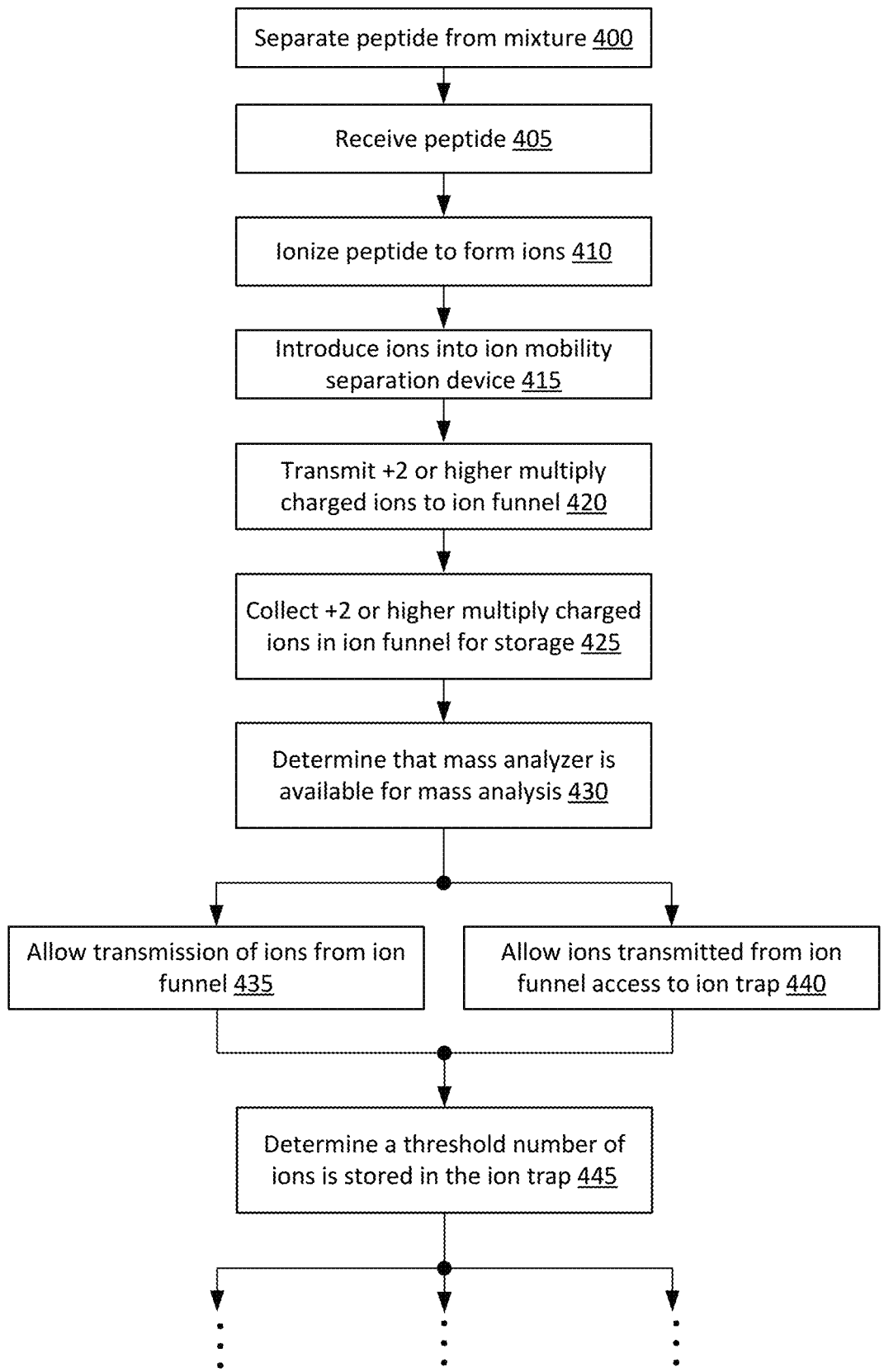
FIGS. 4A and 4B illustrate an example of a block diagram for operating a mass spectrometer using an ion funnel to increase a duty cycle for mass analysis.
Figure 4B:
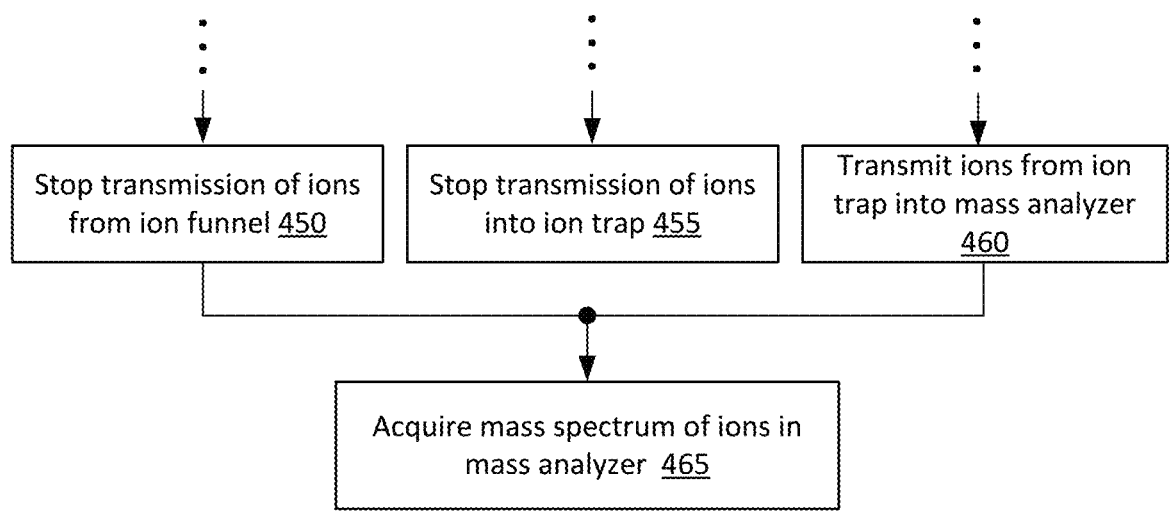
Figure 5:
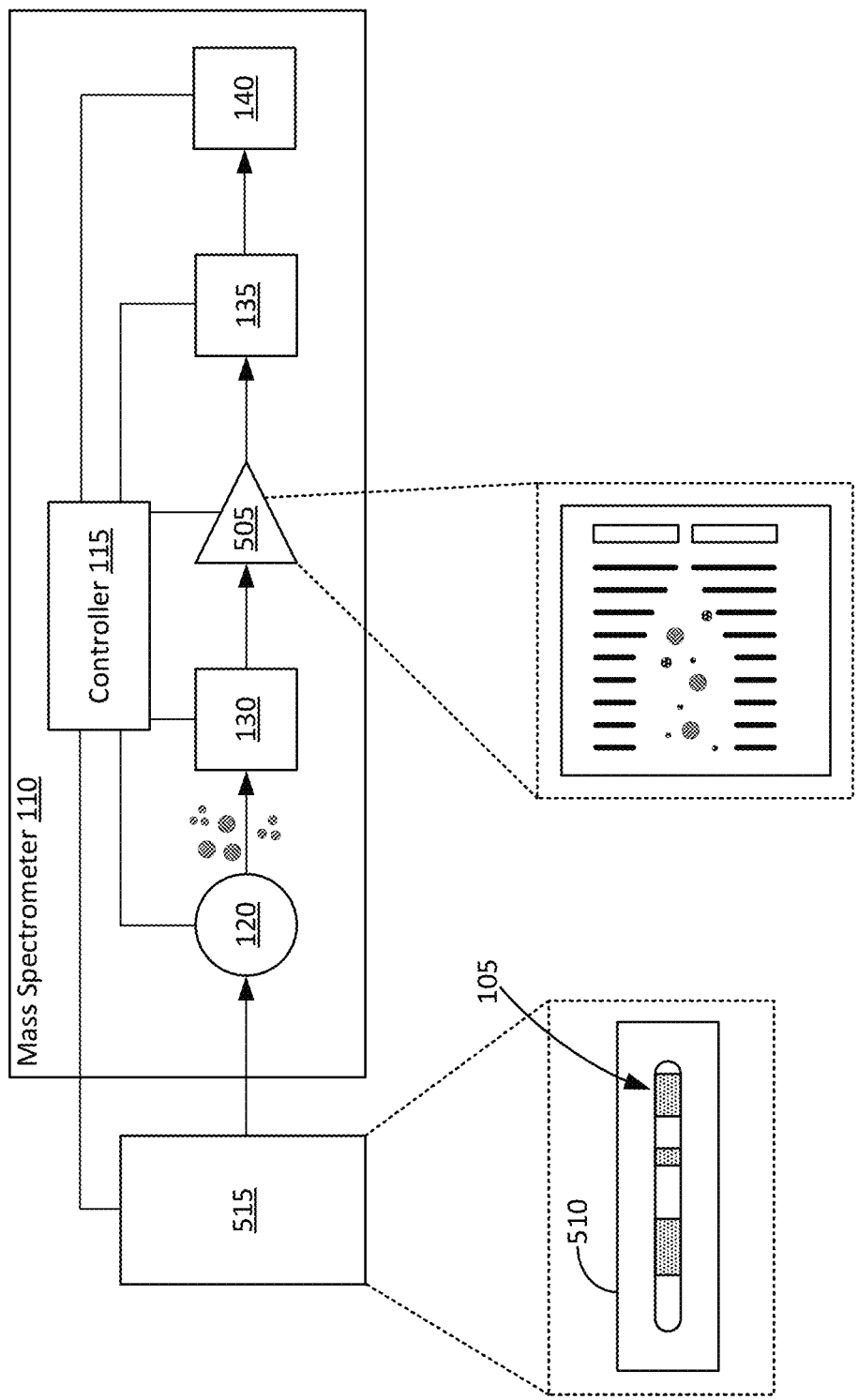
FIG. 5 illustrates an example of a mass spectrometer using an ion funnel to increase a duty cycle for mass analysis.

Further improving the duty cycle can be accomplished by storing the multiply charged ions transmitted through ion mobility separation device 130 within an accumulator positioned upstream in the ion path of the storage trap. FIGS. 4A and 4B illustrate an example of a block diagram for operating a mass spectrometer using an accumulator in the form of an ion funnel to increase a duty cycle for mass analysis. FIG. 5 illustrates an example of a mass spectrometer using an accumulator in the form of an ion funnel to increase a duty cycle for mass analysis.

In FIG. 4A, a peptide is separated from a mixture (400) and received by an ion source of a mass spectrometer (405) to be ionized to form ions (410). This is depicted in FIG. 5, in which LC system 515 separates various peptides of a mixture such that they are separated in space, or position, along a flow path (e.g., within a chromatographic column) such that peptide 105 is introduced into ion source 120 at a different time than other peptides.

Returning to FIG. 4A, the ions formed by the ion source are then introduced into an ion mobility separation device (415). For example, in FIG. 5, ion mobility separation device 130 can implement FAIMS to filter out the singly charged ions but allow transmission of multiply charged ions by using CVs within an appropriate CV range. In FIG. 4A, the multiply charged ions are then stored in an ion funnel (420). For example, in FIG. 5, ion funnel 505 is disposed, or positioned, following ion mobility separation device 130 but before ion trap 135 (which can include storage trap 136 in FIG. 1). Ion funnel 505 is a device used to focus the ions produced from ion source 120 and that are transmitted through ion mobility separation device 130 into a beam using a series of ring electrodes having progressively smaller (in the direction of axial ion motion) apertures and application of RF signals to radially confine ions for efficient transfer to other components within mass spectrometer 110.

In FIG. 4A, the multiply charged ions are then stored in the ion funnel (425). In FIG. 5, by adjusting a DC voltage applied at an electrode at the endpoint of ion funnel 505 (e.g., an electrode near or at the outlet of ion funnel 505), ion funnel can act as a confining device to maintain the ions within a potential well and not be allowed to transmit to ion trap 135. Though an ion funnel described in this example, other types of ion storage devices can be used as the ion accumulator. For example, the accumulator may take the form of a ring trap having cylindrical ring electrodes without the decreasing diameter as used in an ion funnel, a quadrupole or multipole ion guide having elongated rod electrodes, or other types of devices that can accumulate and selectively release ions. In some implementations, the accumulator may be used together with an ion funnel, which provides focusing of ions released by the accumulator.

Next, in FIG. 4A, the controller of the mass spectrometer determines that the mass analyzer is available for mass analysis (430). In FIG. 5, controller 115 determines that orbital electrostatic trap 140 is available for mass analysis (e.g., by determining that an elapsed amount of time has passed since the beginning of mass analysis, determining that no new data is being provided via mass analysis, etc.). This results in the controller to provide signals to the various components such that ions are released from the ion funnel (435) and that the released ions are directed into the ion trap (440). For example, the operational state of the ion funnel can be adjusted from accumulating (without releasing) to releasing (while accumulating) ions by changing a voltage at the electrode of the ion funnel. As a result, ions stored in ion funnel 505 are no longer maintained in an axial potential well, and can exit the device. Meanwhile, controller 115 also adjusts the voltage on split lens 137 such that the ions can transmit into storage trap 136 for storage. That is, the operational state of split lens 137 can be changed from preventing transmission to allowing transmission of ions to storage trap 136. In some implementations, the ion trap can be filled with ions while the orbital electrostatic trap is performing mass analysis.

Next, in FIG. 4A, controller 115 can determine that a threshold number of ions is stored in the ion trap (445). For example, in FIG. 5, ion funnel 505 stores a significantly larger number of charges than storage trap 136, for example, 20e6 elementary charges rather than a relatively lower 2e5 elementary charges that storage trap 136 can store. The ions stored in ion funnel 505 can empty out (i.e., be released towards storage trap 136) relatively fast such that ion funnel 505 would empty in a few hundred microseconds. Thus, by adjusting the voltage of the electrode of ion funnel 505 for a few microseconds (i.e., a short time period in comparison to the overall time needed to empty the entirety of ion funnel 505), a fraction of the stored ions in ion funnel 505 are released, but this small fraction is enough to fill storage trap 136. After this short time period, the voltage on the electrode of ion funnel 505 can be adjusted such that the ions are confined within ion funnel 505 again (450 in FIG. 4B), the voltage applied to split lens 137 is adjusted so that new ions cannot be introduced into storage trap 136 (455 in FIG. 4B), and then the ions stored in storage trap 136 are injected into orbital electrostatic trap 140 for mass analysis (460 in FIG. 4B). Thus, a mass spectrum of the ions in the mass analyzer is acquired (465) using a portion of the ions that were stored in the ion funnel. Meanwhile, any new ions formed by ion source 120 are stored within ion funnel 505.

Controller 115 then determines that mass analysis is complete and, therefore, orbital electrostatic trap 140 is available for mass analysis again. This results in ion funnel being adjusted to allow for ions to transmit through during a short time period again, split lens 137 de-gating to allow ions to enter storage trap 136, and storage trap 136 filling to capacity. Again, the ion funnel is adjusted to store ions without allowing transmission, the split lens 137 prevents ions from entering storage trap 136, and the ions stored within storage trap 136 are injected into orbital electrostatic trap 140 for mass analysis. However, in other implementations, storage trap 136 can be filled with ions while orbital electrostatic trap 140 is performing mass analysis. That is, both storage trap 136 can begin storing ions while orbital electrostatic trap 140 is performing a mass analysis with ions that were previously stored in storage trap 136. Accordingly, the synchronization of operational states of ion funnel 505 (e.g., to switch between storing-only or storing-and-transmitting) and storage trap 136 (e.g., from accepting ions for storage to no longer accepting ions for storage and providing the ions for mass analysis) allows more of the ions being used for mass analysis and, therefore, significantly increasing the duty cycle from 1/60 from the scenario if singly charged ions are not filtered out using ion mobility separation device 130, and also the increasing the duty cycle from ⅙ from the implementation discussed with respect to FIG. 1.

In some implementations, information related to how a peptide is introduced into the mass spectrometer can be used with any of the examples. This information can be used to modify the range of CVs applied to an electrode of a FAIMS, further improving the transmission of multiply charged ions.

For example, due to how a LC system separates peptides within a column, usually (but not always) smaller molecules elute out before larger molecules. Additionally, smaller molecules often have a higher mobility than larger molecules. Thus, the CVs applied to smaller molecules are often different than the CVs applied to larger molecules. For example, a CV of −80 V might be used for a molecule with a higher mobility and a CV of −50 V might be used for a molecule with a lower mobility. Accordingly, peptides that elute from a column and introduced to an ion source earlier in time during the LC process might benefit from increasing the transmission of multiply charged ions from FAIMS by applying a different CV range than peptides that elute from the column at later times.

Figure 6:
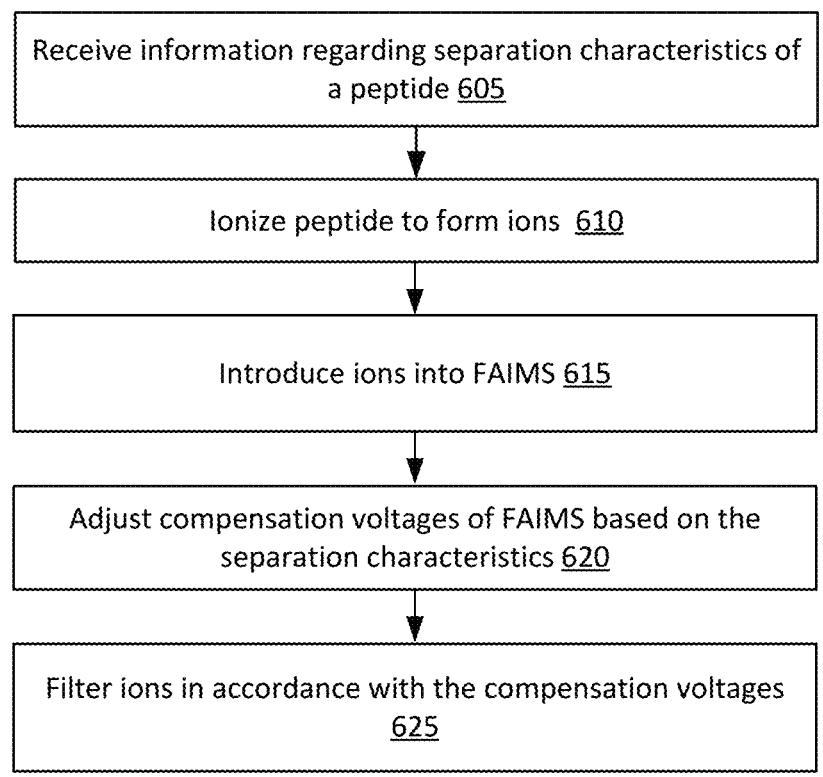
FIG. 6 illustrates an example of a block diagram for adjusting CVs based on separation characteristics of a peptide.

FIG. 6 illustrates an example of a block diagram for adjusting CVs based on separation characteristics of a peptide. In FIG. 6, information regarding separation characteristics of a peptide is received by a controller of a mass spectrometer (605). For example, in FIG. 5, LC system 515 separates peptides in a mixture such that they are introduced into mass spectrometer 110 at different times, as previously discussed. Controller 115 can receive data from LC system 515 regarding the separation process, for example, the retention time of peptide 105 (i.e., the time at from a setpoint in which peptide 105 emerges from column 510), which is different than the retention time of the next peptide to elute from column 510. Alternatively, controller 115 can determine the retention time based on the peptide being introduced to ion source 120.

Returning to FIG. 6, the peptide can be ionized (615) and the ions introduced into a FAIMS device (620). Moreover, the compensation voltages applied to an electrode of the FAIMS device can be selected or adjusted based on the separation characteristics (620). For example, controller 115 can select a CV range based on the retention time of the peptide currently being ionized by ion source 120. Thus, peptide 105 might be ionized, the ions provided to the FAIMS device implemented by ion mobility separation device 120, and the CV voltages applied to electrode 131 (in FIG. 1) might alternate range from −45 V to −75 V. If the retention time was higher (e.g., above a threshold value), then another range might be selected, for example, −50 V to −80 V because the ions formed from the ionization of a peptide eluting at a later retention time would have a higher likelihood of having lower mobilities. Returning back to the block diagram of FIG. 6, the ions are then filtered in accordance with the compensation values (625).

Other separation characteristics that can be considered to adjust compensation voltages can include hydrophobicity of the peptide. In some implementations, multiple characteristics can be considered, for example, both hydrophobicity and retention time.

Figure 7:
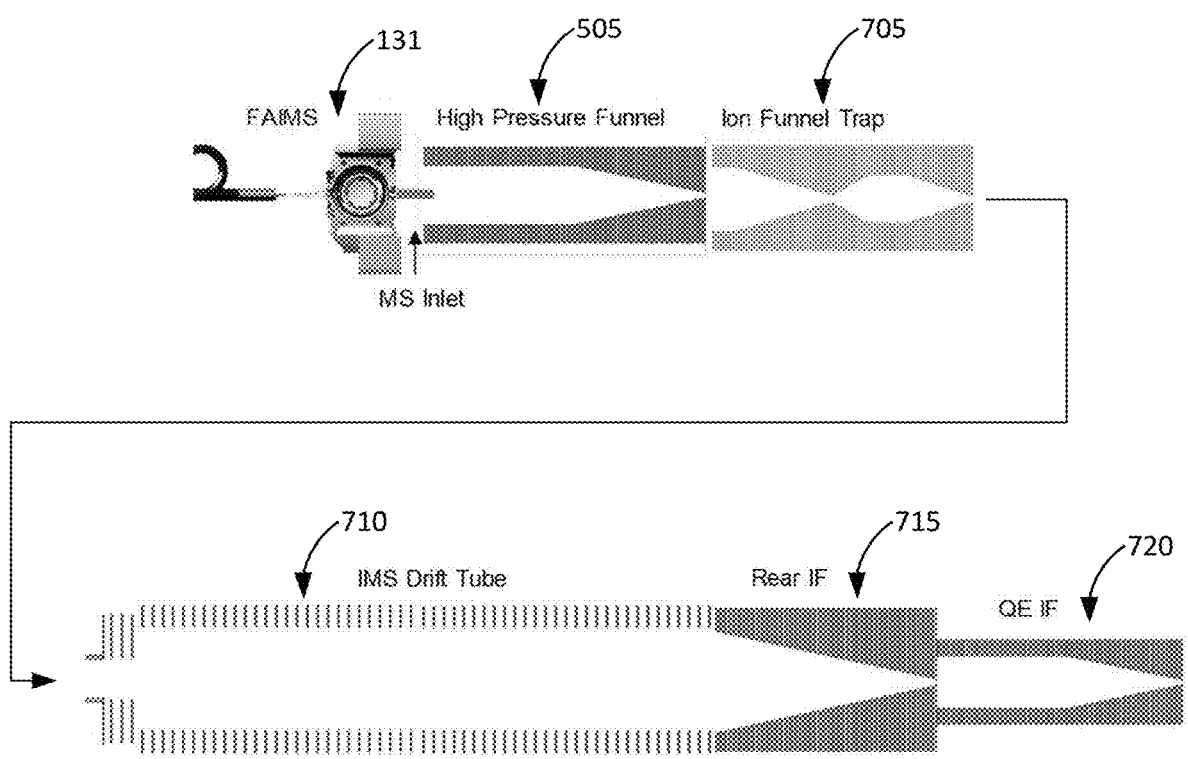
FIG. 7 illustrates an example of a field asymmetric-waveform ion-mobility spectrometer (FAIMS) used with an ion mobility spectrometer (IMS).

FAIMS can be implemented in connection with another IMS device in a mass spectrometer. FIG. 7 illustrates an example of a field asymmetric-waveform ion-mobility spectrometry (FAIMS) device used with an ion mobility spectrometer (IMS). In FIG. 7, FAIMS device 131 is disposed before ion funnel 505, similar to FIG. 5. Ion funnel trap 705 is an additional component that can accumulate and selectively release ions received from ion funnel 505 to IMS device 710. IMS device 710 is employs a different mobility property-based separation technique than FAIMS in that IMS 710 can be a drift-time ion mobility spectrometer (DTIMS) in which smaller ions travel faster through the drift tube than larger ions due to differences in ion mobilities. The ions are separated based on their drift time through the drift tube. Thus, by using a FAIMS device followed by a (drift-tube type) IMS device, additional separation of the ions can be achieved for better mass analysis. In some implementations, IMS 710 can be implemented with a Structures for Lossless Ion Manipulations (SLIM) device, as described in Ibrahim et al, "New Frontiers for Mass Spectrometry based upon Structures for Lossless Ion Manipulations", Analyst, vol. 142, pp. 1010-1021 (2017) and Ibrahim et al., "Ion Elevators and Escalators in Multilevel Structures for Lossless Ion Manipulations", Analytical Chemistry, vol. 89, pp. 1972-1977 (2017). By using a SLIM device, the voltages used by FAIMS 131 do not have to be floated upon the voltages used by IMS 710. Rather, the voltages used by FAIMS 131 can be offset by the maximum voltage used by IMS 710, providing an easy implementation of the power supplies.

As depicted in FIG. 7, rear ion funnel 715 receives the ions transmitting through IMS 710 before the ions are then further transmitted to ion funnel 720, which can be an ion funnel positioned at an inlet of a mass spectrometer, though ion funnel 720 need not be necessarily implemented. Thus, the ions are ionized, filtered using FAIMS, and then further separated using IMS device 710, which can be a drift tube separating ions into groups of similar mobilities that are sequentially transmitted. Not only does this provide more separation of the ions, but performing FAIMS first can allow for solvent clusters to shed off the ions due to the movement of the ions and internal heating generated through FAIMS. By shedding off the solvent clusters using FAIMS, better separation through IMS 710 can be achieved. Thus, if performing top-down proteomics with proteins, better results are achieved.

Figure 8:
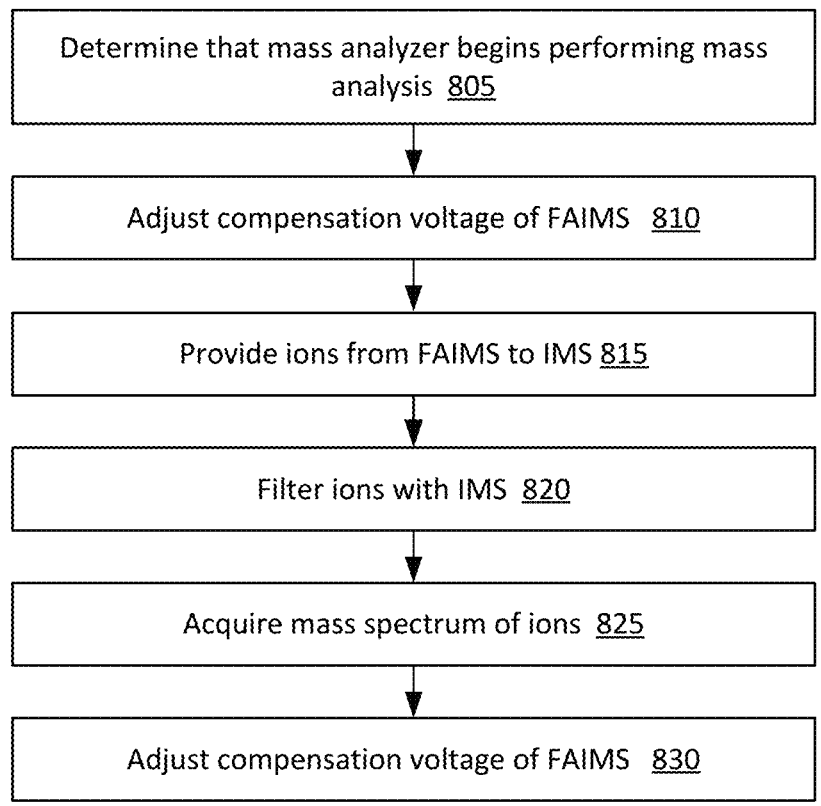
FIG. 8 illustrates an example of a block diagram for using FAIMS with IMS.

Using FAIMS and IMS with a mass spectrometer with orbital electrostatic trap 140 involves synchronizing the various components. FIG. 8 illustrates an example of a block diagram for using the FAIMS device with an IMS device. In FIG. 8, a mass analyzer begins a mass analysis (805). For example, ions can be injected from a storage trap into an orbital electrostatic trap for mass analysis. This is caused by changing the voltages used by the storage trap to store ions and causing injection of the ions into the orbital electrostatic trap, as previously discussed. Thus, the changing of one or more voltages at this point is indicative of the beginning of a mass analysis to be performed by the orbital electrostatic trap.

Another component (e.g., controller 115, or FAIMS 131 or IMS 710) can determine that the mass analysis has started. Thus, FAIMS 131 might be instructed to change the CV (810) such that different ions are stored in ion funnel 505. IMS 710 might also be instructed to begin separating ions in accordance with their ion mobility (815). Eventually, the ions are filtered through the IMS 710 (820) and stored into the storage trap via the split lens. Thus, while the orbital electrostatic trap is performing mass analysis of ions that were transmitted through FAIMS 131 at one CV, another set of ions that were transmitted through FAIMS 131 at another CV are being stored in the storage trap. When the first mass analysis is complete, the ions in the storage trap can then be injected into the orbital electrostatic trap for a new mass spectrum to be acquired (825). When the new mass analysis is begun, the CV of FAIMS can be adjusted again (830).

Many of the examples describe implementations with liquid chromatography (LC) for separating peptides. However, other types of mixture separation can be used including gas chromatography (GC) or capillary electrophoresis (CE).

The examples describe techniques for peptides, however, other biomolecules can be used with the techniques described herein. For example, in addition to proteins and their peptides, other types of biomolecules that can be used with the techniques include lipids, nucleic acids, metabolites, oligosaccharides, polysaccharides, and the like. Moreover, other large molecules other than biomolecules can be used, in addition to small molecules.

The examples described herein include using an orbital electrostatic trap mass analyzer, but other mass analyzers can also be used with the techniques. For example, quadrupole or time-of-flight (TOF) analyzers might be used. In another example, a tandem mass spectrometer might be used.

Figure 9:
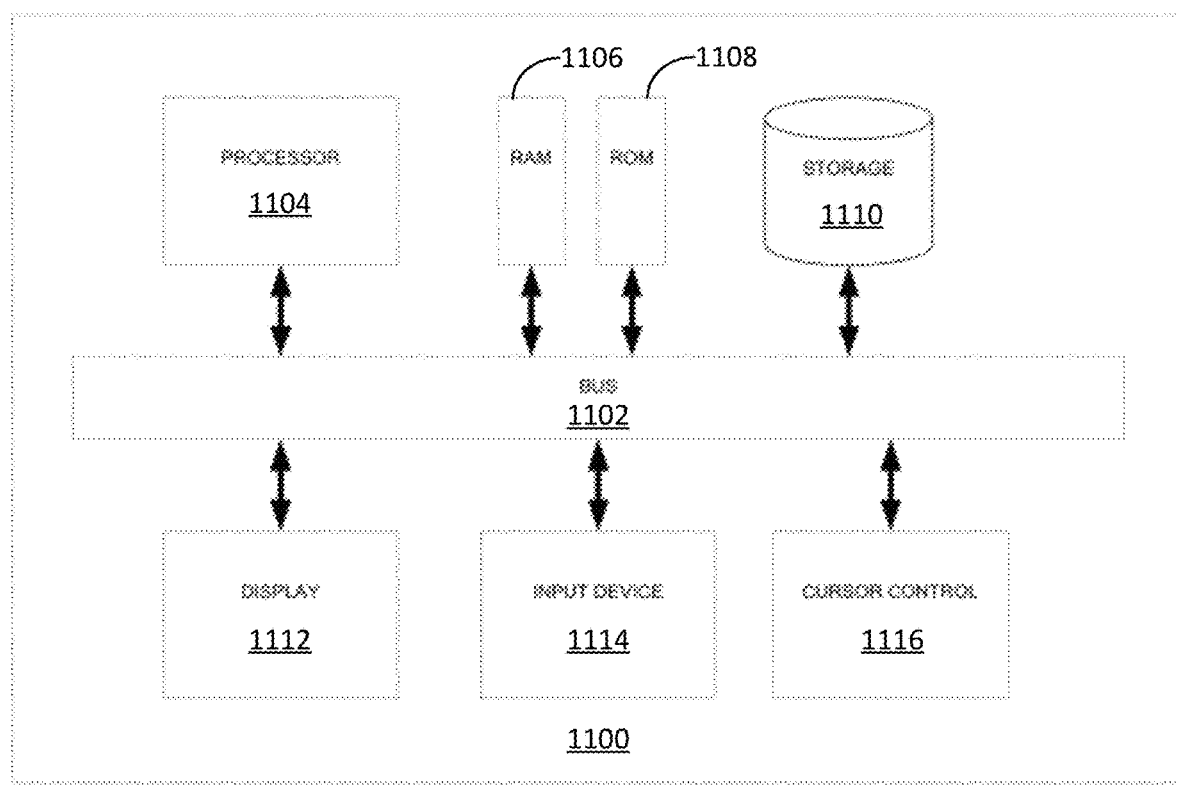
FIG. 9 illustrates an example of an electronic device which may be used to implement some of the examples.

FIG. 9 illustrates an example of an electronic device which may be used to implement some of the implementations. In some implementations, the electronic device of FIG. 9 can store or use a computer program product including one or more non-transitory computer-readable media having computer programs instructed stored therein, the computer program instructions being configured such that, when executed by one or more computing devices, the computer program instructions cause the one or more computing devices to perform he techniques described herein.

In FIG. 9, computer system 1100 can implement any of the methods or techniques described herein. For example, computer system 1100 can implement controller 115 in FIG. 1. Thus, the operation of components of the associated mass spectrometer may be adjusted in accordance with calculations or determinations made by computer system 1100. In various embodiments, computer system 1100 can include a bus 1102 or other communication mechanism for communicating information, and a processor 1104 coupled with bus 1102 for processing information. In various embodiments, computer system 1100 can also include a memory 1106, which can be a random-access memory (RAM) or other dynamic storage device, coupled to bus 1102, and instructions to be executed by processor 1104. Memory 1106 also can be used for storing temporary variables or other intermediate information during execution of instructions to be executed by processor 1104. In various embodiments, computer system 1100 can further include a read only memory (ROM) 1108 or other static storage device coupled to bus 1102 for storing static information and instructions for processor 1104. A storage device 1110, such as a magnetic disk or optical disk, can be provided and coupled to bus 1102 for storing information and instructions.

In various embodiments, computer system 1100 can be coupled via bus 1102 to a display 1112, such as a cathode ray tube (CRT) or liquid crystal display (LCD), for displaying information to a computer user. An input device 1114, including alphanumeric and other keys, can be coupled to bus 1102 for communicating information and command selections to processor 1104. Another type of user input device is a cursor control 1116, such as a mouse, a trackball or cursor direction keys for communicating direction information and command selections to processor 1104 and for controlling cursor movement on display 1112. This input device typically has two degrees of freedom in two axes, a first axis (i.e., x) and a second axis (i.e., y), that allows the device to specify positions in a plane.

A computer system 1100 can perform the techniques described herein. Consistent with certain implementations, results can be provided by computer system 1100 in response to processor 1104 executing one or more sequences of one or more instructions contained in memory 1106. Such instructions can be read into memory 1106 from another computer-readable medium, such as storage device 1110. Execution of the sequences of instructions contained in memory 1106 can cause processor 1104 to perform the processes described herein. In various embodiments, instructions in the memory can sequence the use of various combinations of logic gates available within the processor to perform the processes describe herein. Alternatively hard-wired circuitry can be used in place of or in combination with software instructions to implement the present teachings. In various embodiments, the hard-wired circuitry can include the necessary logic gates, operated in the necessary sequence to perform the processes described herein. Thus implementations described herein are not limited to any specific combination of hardware circuitry and software.

The term "computer-readable medium" as used herein refers to any media that participates in providing instructions to processor 1104 for execution. Such a medium can take many forms, including but not limited to, non-volatile media, volatile media, and transmission media. Examples of non-volatile media can include, but are not limited to, optical or magnetic disks, such as storage device 1110. Examples of volatile media can include, but are not limited to, dynamic memory, such as memory 1106. Examples of transmission media can include, but are not limited to, coaxial cables, copper wire, and fiber optics, including the wires that comprise bus 1102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, etc.

While the techniques are described in conjunction with various implementations or embodiments, it is not intended that the techniques be limited to such embodiments. On the contrary, the techniques encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general-purpose computer selectively activated or configured by a computer program stored in the computer. In particular, various general-purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

We claim:

1. An apparatus for analyzing a peptide-containing biological sample, comprising:
    a chromatography device configured to temporally separate components of the biological sample;
    an electrospray ionization (ESI) source configured to receive a component separated from the biological sample and generate singly-charged ions and multiply-charged ions from the component;
    a field asymmetric-waveform ion-mobility spectrometry (FAIMS) device configured to receive the singly-charged ions and the multiply-charged ions, and preferentially transmit multiply-charged ions;
    an ion accumulator arranged to receive and confine the ions transmitted by the FAIMS device;
    a storage trap configured to receive the ions released from the ion accumulator and store the released ions, the storage trap having a lower storage capacity than the ion accumulator;
    a mass analyzer configured to receive the ions stored in the storage trap for mass analysis; and
    a controller circuit configured to adjust operation of the accumulator to allow release a portion of the ions confined therein to the storage trap.

2. The apparatus of claim 1, wherein the storage trap is a curved linear ion trap, and the mass analyzer is an orbital electrostatic trap mass analyzer.

3. The apparatus of claim 1, wherein the ion accumulator is an ion funnel.

4. A mass spectrometer, comprising:
    an ion source configured to receive a sample and generate singly-charged ions and multiply-charged ions from the sample;
    an ion-mobility spectrometer (IMS) configured to receive the singly-charged ions and the multiply-charged ions, and configured to allow transmission of more multiply-charged ions through an output of the IMS than transmission of the singly-charged ions through the output of the IMS;
    an ion accumulator configured to store the multiply-charged ions that drift through the output of the IMS;
    a storage trap configured to receive a portion of the multiply-charged ions stored by the ion accumulator;
    a mass analyzer configured to receive the portion of multiply-charged ions stored in the storage trap for mass analysis; and
    a controller circuit configured to determine an operational state of the mass analyzer and adjust operation of the ion accumulator to allow the portion of the multiply-charged ions to transmit from the ion storage to the storage trap.

5. The mass spectrometer of claim 4, wherein the storage trap is a curved linear ion trap, and the mass analyzer is an orbital electrostatic trap mass analyzer.

6. The mass spectrometer of claim 4, wherein the IMS is a field asymmetric-waveform ion-mobility spectrometer (FAIMS), and the transmission of the multiply-charged ions through the output is based on an application of a range of compensation voltages (CVs) applied to an electrode of the FAIMS that causes the multiply-charged ions to drift through to the output without impacting an electrode of the FAIMS and causes the singly-charged ions to impact an electrode of the FAIMS without drifting through the output.

7. The mass spectrometer of claim 4, wherein the ion accumulator is an ion funnel.

8. The mass spectrometer of claim 7, wherein the operational state of the mass analyzer is one of: currently performing mass analysis, or available to perform mass analysis, and wherein the operation of the ion funnel is adjusted to store the multiply-charged ions without transmitting the multiply-charged ions from the ion funnel to the ion trap when the operational state of the mass analyzer is currently performing mass analysis, and the operation of the ion funnel is adjusted to store the multiply-charged ions while allowing transmitting of the multiply-charged ions from the ion funnel to the ion trap when the operational state of the mass analyzer is available to perform mass analysis.

9. The mass spectrometer of claim 4, wherein the controller circuit is configured to allow transmission of the portion of the multiply-charged ions stored in the ion accumulator to the storage trap based on a determination of the operational state of the mass analyzer indicating that the mass analyzer is available to perform mass analysis.

10. The mass spectrometer of claim 9, wherein the ion accumulator is an ion funnel.

11. The mass spectrometer of claim 4, further comprising:
    a separation device configured to separate the sample from a mixture, wherein the controller circuit is further configured to determine information related to how the sample is separated from the mixture, and wherein the controller is configured to adjust operational parameters of the IMS based on the determination of the information related to how the sample is separated from the mixture.

12. The mass spectrometer of claim 11, wherein the IMS is a field asymmetric-waveform ion-mobility spectrometer (FAIMS), and the operational parameters are compensation voltages (CVs) applied to an electrode of the FAIMS.

13. The mass spectrometer of claim 4, further comprising: a chromatography system configured to separate the sample from a mixture, wherein the controller circuit is further configured to determine a retention time of the sample, and wherein the controller is configured to adjust operational parameters of the IMS based on the determination of the retention time of the sample.

14. The mass spectrometer of claim 4, wherein the chromatography system is a liquid chromatography (LC) system.

15. A method of operating a mass spectrometer to analyze a biological sample, comprising:
ionizing a sample to generate singly-charged ions and multiply-charged ions from the biological sample;
transmitting more of the multiply-charged ions than the singly-charged ions;
storing the multiply-charged ions in an ion accumulator, the ion accumulator storing more multiply-charged ions than singly-charged ions;
determining that a mass analyzer is available to perform mass analysis;
transmitting a portion of the multiply-charged ions from the ion accumulator to a storage trap based on the determination that the mass analyzer is available to perform mass analysis;
injecting the portion of the multiply-charged ions from the storage trap to the mass analyzer; and
performing a mass analysis of the portion of the multiply-charged ions.

16. The method of claim 15, wherein transmitting more of the multiply-charged ions than the singly-charged ions includes:
receiving, with a field asymmetric-waveform ion-mobility spectrometer (FAIMS), the singly-charged ions and the multiply-charged ions; and
applying a range of compensation voltages (CVs) to an electrode of the FAIMS to cause the multiply-charged peptide ions to drift through to the output without impacting an electrode of the FAIMS and causes the singly-charged peptide ions to impact an electrode of the FAIMS without drifting through the output.

17. The method of claim 15, wherein the biological sample is a mixture of peptides.

18. The method of claim 15, the mass analyzer is an orbital electrostatic trap mass analyzer.

19. The method of claim 15, wherein the ion accumulator is an ion funnel.

20. The method of claim 15, wherein the storage trap is a curved linear ion trap.

* * * * *